(12) United States Patent
Durand

(10) Patent No.: US 10,694,991 B2
(45) Date of Patent: *Jun. 30, 2020

(54) LOW FREQUENCY NON-INVASIVE SENSORIAL STIMULATION FOR SEIZURE CONTROL

(71) Applicant: CASE WESTERN RESERVE UNIVERSITY, Cleveland, OH (US)

(72) Inventor: Dominique Durand, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 358 days.

This patent is subject to a terminal disclaimer.

(21) Appl. No.: 15/788,208

(22) Filed: Oct. 19, 2017

(65) Prior Publication Data

US 2018/0035939 A1    Feb. 8, 2018

Related U.S. Application Data

(63) Continuation of application No. 14/683,197, filed on Apr. 10, 2015, now Pat. No. 9,955,907.

(Continued)

(51) Int. Cl.
*A61M 21/00*     (2006.01)
*A61B 5/00*      (2006.01)
(Continued)

(52) U.S. Cl.
CPC .......... *A61B 5/4094* (2013.01); *A61B 5/0476* (2013.01); *A61B 5/04842* (2013.01);
(Continued)

(58) Field of Classification Search
CPC .... A61B 5/4076; A61B 5/4094; A61B 5/4842
(Continued)

(56) References Cited

U.S. PATENT DOCUMENTS 3,967,616 A    7/1976  Ross
5,304,112 A    4/1994  Mrklas et al.
(Continued)

OTHER PUBLICATIONS

Couturier, N. et al., (2013), Auditive and visual sensorial stimulation is able to suppress seizure frequency in two animal models of epilepsy. (manuscript in preparation).
(Continued)

*Primary Examiner* — John P Lacyk
(74) *Attorney, Agent, or Firm* — Tarolli, Sundheim, Covell & Tummino LLP

(57) ABSTRACT

Example apparatus and methods reduce epileptic seizures in a human patient by non-invasively providing low frequency (e.g., 1-10 Hz) audio stimuli coordinated with low frequency (e.g., 1-10 Hz) visual stimuli to the patient. The signals are provided non-invasively through the eyes and ears. The audio stimuli and visual stimuli may be selected or coordinated based on a state (e.g., hyperexcitability, imminent epileptic seizure, epileptic seizure in progress, REM sleep) determined from an EEG signal acquired from the patient. Apparatus for delivering the audio stimuli and visual stimuli may be incorporated into a single wearable apparatus (e.g., glasses with earphones, hat, headband). The single wearable apparatus may also provide noise cancellation and visual stimulus diminution. The audio stimuli may be incorporated into music or random background noise.

20 Claims, 6 Drawing Sheets

Related U.S. Application Data

(60) Provisional application No. 61/983,105, filed on Apr. 23, 2014.

(51) Int. Cl.
*A61B 5/0476* (2006.01)
*A61B 5/0484* (2006.01)
*A61N 5/06* (2006.01)

(52) U.S. Cl.
CPC ......... *A61B 5/04845* (2013.01); *A61M 21/00* (2013.01); *A61N 5/0622* (2013.01); *A61B 5/4812* (2013.01); *A61B 5/6803* (2013.01); *A61B 5/6898* (2013.01); *A61B 5/7203* (2013.01); *A61M 2021/0027* (2013.01); *A61M 2021/0033* (2013.01); *A61M 2021/0044* (2013.01); *A61M 2230/10* (2013.01); *A61N 2005/0647* (2013.01); *A61N 2005/0648* (2013.01)

(58) Field of Classification Search
USPC ....................................................... 600/26–28
See application file for complete search history.

(56) References Cited

U.S. PATENT DOCUMENTS

| | | |
|---|---|---|
| 5,577,990 A | 11/1996 | Widjaja et al. |
| 6,591,138 B1 | 7/2003 | Fischell et al. |
| RE39,539 E | 4/2007 | Torch |
| 2009/0082691 A1 | 3/2009 | Denison et al. |

OTHER PUBLICATIONS

Hughes, J. R. et al., "The "Mozart effect" on epileptiform activity." Clinical Electroencephalography 29.3 (1998): 109-119.
Kile et al., "Low frequency stimulation decreases seizure activity in a mutation model of epilepsy." Epilepsia 51.9 (2010): 1745-1753.
Koubeissi et al., "Low Frequency Electrical Stimulation of White Matter Tracts in intractable Mesial Temporal Lobe Epilepsy (IN5-1.010)." Neurology 78.1 Supplement (2012): IN5-1.
Lerner, Y. et al., "Eyes wide shut: amygdala mediates eyes-closed effect on emotional experience with music." PLoS One 4.7 (2009): e6230.
Lin, L, et al., Mozart K.545 Mimics K.448 in Reducing Epileptiform Discharges in Epileptic Children (2012).
Lin, L. et al., "Mozart K. 448 acts as a potential add-on therapy in children with refractory epilepsy." Epilepsy & Behavior 20.3 (2011): 490-493.
Lin, L. et al., "Mozart K. 448 and epileptiform discharges: effect of ratio of lower to higher harmonics." Epilepsy research 89.2 (2010): 238-245.
Lin, L. et al., "The long-term effect of listening to Mozart K. 448 decreases epileptiform discharges in children with epilepsy." Epilepsy & Behavior 21.4 (2011): 420-424.
Meinecke, F. C. et al., "Measuring phase synchronization of superimposed signals." Physical Review Letters 94.8 (2005): 084102.
Menkes, D. L. et al., "Slow-Frequency Repetitive Transcranial Magnetic Stimulation in a Patient with Focal Cortical Dysplasia," Epilepsia 41.2 (2000): 240-242.
Rashid, S. et al., "Low frequency stimulation of ventral hippocampal commissures reduces seizures in a rat model of chronic temporal lobe epilepsy." Epilepsia 53.1 (2012): 147-156.

LOW FREQUENCY NON-INVASIVE SENSORIAL STIMULATION FOR SEIZURE CONTROL

CROSS-REFERENCE TO RELATED APPLICATIONS

This application is a continuation of U.S. patent application Ser. No. 14/683,197 filed 10 Apr. 2015, which claims the benefit of U.S. Provisional Patent Application No. 61/983,105 filed 23 Apr. 2014 (Now Expired). All of the above-identified applications are incorporated herein by reference in their entireties for all purposes.

BACKGROUND

Epilepsy is a devastating neurological disease that affects more than three million Americans and fifty million people worldwide. There are more people with epilepsy than multiple sclerosis, cerebral palsy, muscular dystrophy and Parkinson's disease combined. Epilepsy takes more lives than breast cancer. In over thirty percent of patients, seizures are not controlled, even with state of the art medical treatments. The cognitive and emotional lives of many patients are constantly being disrupted. Improvements in treatments have come slowly as scientists have learned more about the physiological changes underlying epilepsy and have developed new methods for modifying brain activity.

Current therapy for drug resistant patients with epilepsy is surgery. However, surgery may only be appropriate for patients that have an identified single focus and for patients with a focus that is located in areas of the brain that can be resected with acceptable side effects. New alternative treatments offer hope to patients who have not had success with existing drugs. These alternative treatments include vagal nerve stimulation (VNS), deep brain electrical stimulation (DBS), or trans-cranial magnetic stimulation (TMS). These procedures may send pulses of energy at constant amplitude and frequency to control excessive brain wave activity.

These procedures may use low frequency (1-10 Hz) stimulus in order to entrain the network. Low frequency stimulation has been shown to reduce seizure frequency. For example, techniques including DBS, cortical electrical stimulation, VNS and TMS have produced seizure reduction in human subjects.

BRIEF DESCRIPTION OF THE DRAWINGS

The accompanying drawings, which are incorporated in and constitute a part of the specification, illustrate various example devices, methods, apparatus and other embodiments of various aspects of the invention. It will be appreciated that the illustrated element boundaries (e.g., boxes, groups of boxes, or other shapes) in the figures represent one example of the boundaries. In some embodiments one element may be designed as multiple elements, multiple elements may be designed as one element, an element shown as an internal component of another element may be implemented as an external component and vice versa, and so on. Furthermore, elements may not be drawn to scale.

DETAILED DESCRIPTION

Example apparatus and methods reduce epileptic seizures in a human patient by non-invasively providing low frequency (e.g., 1-10 Hz) audio stimuli coordinated with low frequency (e.g., 1-10 Hz) visual stimuli to the patient. The signals are provided non-invasively through the eyes and ears. Non-invasively means using the senses of sight and hearing through the eyes and ears without using an implanted electrode to electrically stimulate a nerve. The audio stimuli and visual stimuli may be selected or coordinated based on a state (e.g., hyperexcitability, imminent epileptic seizure, epileptic seizure in progress, rapid eye movement (REM) sleep) determined from an electroencephalogram (EEG) signal acquired from the patient. Apparatus for delivering the audio stimuli and visual stimuli may be incorporated into a single wearable apparatus (e.g., glasses with earphones, hat, headband). The single wearable apparatus may also provide noise cancellation and visual stimulus diminution. The audio stimuli may be incorporated into music or random background noise. Coordinating the audio stimuli and visual stimuli may include providing only audio stimuli or visual stimuli but not both.

Figure 1:
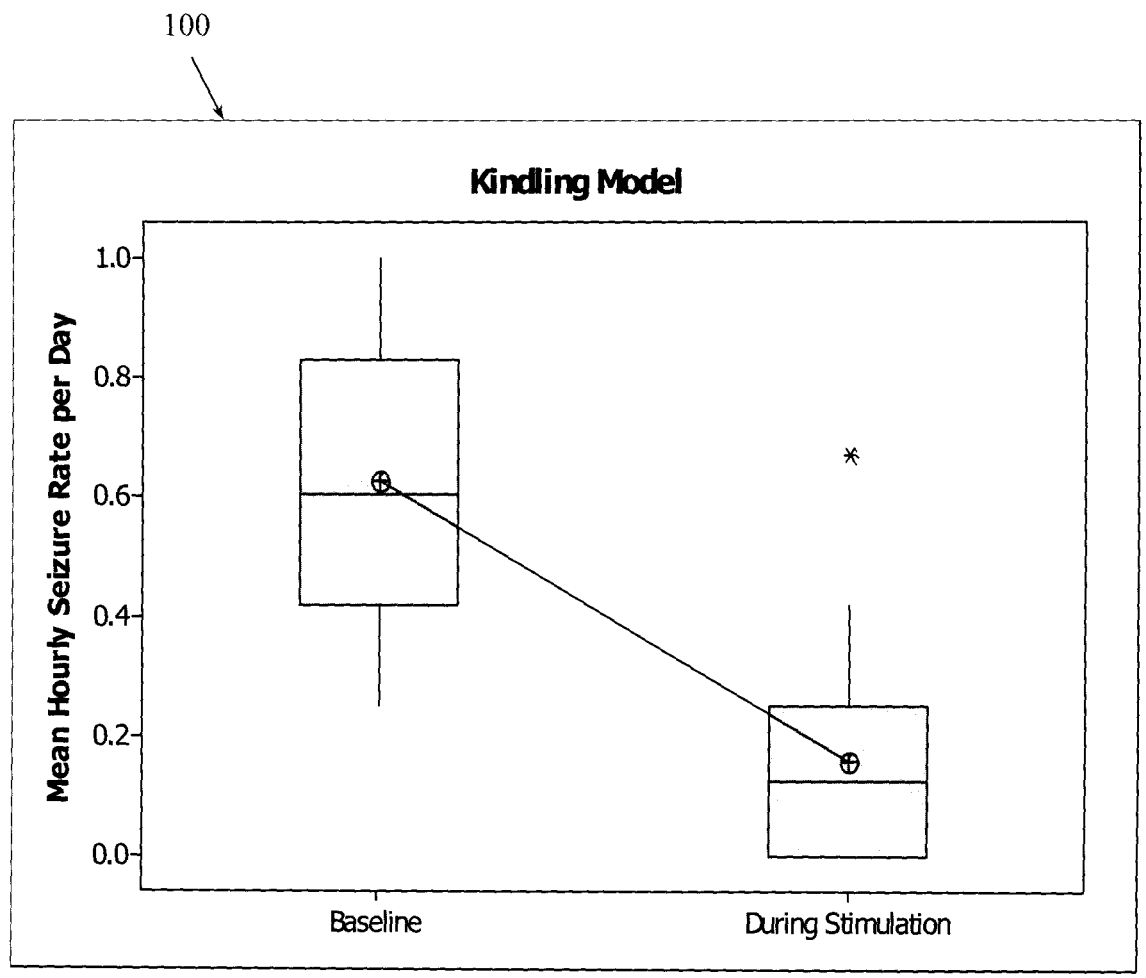
FIG. 1 illustrates the results of a non-invasive stimulation study using example apparatus and methods in rats.

Example apparatus and methods perform combined visual and auditory stimulation at low frequency (1-10 Hz) using electrical currents, optogenetic stimulus, and sensorial stimulation to reduce seizure frequency by seventy to ninety percent. Optogenetic stimulus may include neural stimulation in genetically modified light sensitive neurons. FIG. 1 illustrates the results of a non-invasive stimulation study using example apparatus and methods in rats. In one embodiment, a combination of click sounds and short white light pulses delivered at 1 Hz induced a 70% reduction of seizure frequency in two different animal models of epilepsy. In one experiment, rats were exposed to visual and auditory clicks for twelve hours per day for a week. 70% reduction was observed for the kindling model (Rashid and Durand 2012) of epilepsy, which showed that low frequency stimulation of ventral hippocampal commissures reduces seizures in a rat model of chronic temporal lobe epilepsy. 50% reduction was observed in the kainic acid model.

Auditory stimulation has been demonstrated to be effective at controlling seizures. In one study, twenty-three of twenty-nine patients with focal discharges or bursts of generalized spike and wave complexes who listened to the Mozart piano sonata K448 showed significant decreases in epileptiform activity. Similarly, listening to the Mozart piano sonata was effective in 8/11 patients with refractory epilepsy. Listening to the sonata had antiepileptic long lasting effects in eighty children for six months. The spectrum of Mozart K448 published by the Taiwanese group is 1 Hz. While auditory stimulation alone may produce positive results, example apparatus and methods employ a combined visual and auditory approach to produce superior results.

Deep Brain Stimulation (DBS) and Vagal Nerve Stimulation (VNS) require surgery that is inherently disruptive of the brain and body integrity. Transcranial magnetic stimulation (TMS) is difficult to deliver to outpatients and is not yet available for daily home applications. Example apparatus and methods that employ combined visual and auditory low frequency sensorial stimulation (LFSS) facilitate applying principles of phase synchronization while avoiding the requirement of surgery or the use of bulky or expensive equipment. LFSS is simply and flexibly applied using, for example, an open loop system. Example apparatus and methods may be configurable to allow the audio or visual elements of LFSS to be adapted to patient age or preferences. For example, some patients may prefer to listen to a first type of music (e.g., classical) while other patients may prefer to listen to a second type of music (e.g., pop). LFSS may be suitable as an adjuvant to anti-epileptic medication for all patients with epilepsy. LFSS may be particularly suitable for children for whom DBS is not recommended and for whom VNS may not be effective.

Example LFSS may be implemented with a device having a sleeping mask for the eyes, ear phones, EEG electrodes, and an electronic processing unit More generally an LFSS system may include a visual signal output device, an audio signal output device, a monitor apparatus, and an audio/visual signal production apparatus. The eye mask may be designed on a per patient basis, for populations (e.g., adults, children), or in other ways. The eye mask may be designed to reduce the spectrum of stimulation presented to the eyes to just the intended sensorial stimulation. The eye mask may be dark, comfortable, and may have enough clearance between the mask shell and the eyelids to avoid eye blink frictions. Light emitting components (e.g., LEDS, infrared emitters) may be embedded or otherwise associated with the mask to emit, for example, a low intensity glow that can penetrate the eyelids. Earphones may be designed to eliminate external inputs, which may be referred to as performing noise cancellation. Noise cancellation may be employed since listening to music with closed eyes increases the general activation of sensorial and limbic areas of the brain. The earphones may be plugged into or otherwise operably connected to a sound generating device. The sound generating device may be, for example, a small computer capable of playing high quality stereo music. The device may be, for example, an MP3 player (e.g., iPod®).

A computer, circuit, or other apparatus or control process may synchronize light production/delivery and sound production/delivery. EEG electrodes may record the seizure activity for the patient. In different embodiments, the EEG electrodes may be placed next to or on the ear phones. In one embodiment, the audio signal device may provide music with embedded "clicks". The music may have a tempo between, for example, 1 and 10 Hz. Music tracks may be composed directly for LFSS or may be arranged by adding some low frequency sounds synchronized to the original tempo to an already existing track. In one embodiment, random noise with added clicks or short tones may be employed.

In one embodiment, the components may be arranged in an open loop. The components may include just the audio/visual stimulation system. In one embodiment, the duration, timing, frequency, or other parameters of the stimulation may be programmed by a physician and implemented in a computer that provides or controls the stimuli. As computing power has become ever more miniaturized, the computer may be, for example, a smart phone, PDA, or other small (e.g., portable) device placed next to the patient. In one embodiment, the computer may be integrated into a wearable article.

In one embodiment, the components may also include EEG equipment. The EEG equipment (e.g., electrodes, monitoring circuit) may track seizure activity (e.g., number of seizures, duration of seizures, intensity of seizures) for the patient. In one embodiment, seizure detection may monitor the success of the therapy. The EEG signal may, for example, be stored on the computer, be transmitted to a treating neurologist, or be provided to other monitoring personnel or processes.

In one embodiment, the system may operate in a closed loop to match the stimuli to a particular condition of the patient. For example, stimulation may be selectively applied during REM sleep or when interictal activity within the EEG indicates hyperexcitibility in the brain.

Figure 2:
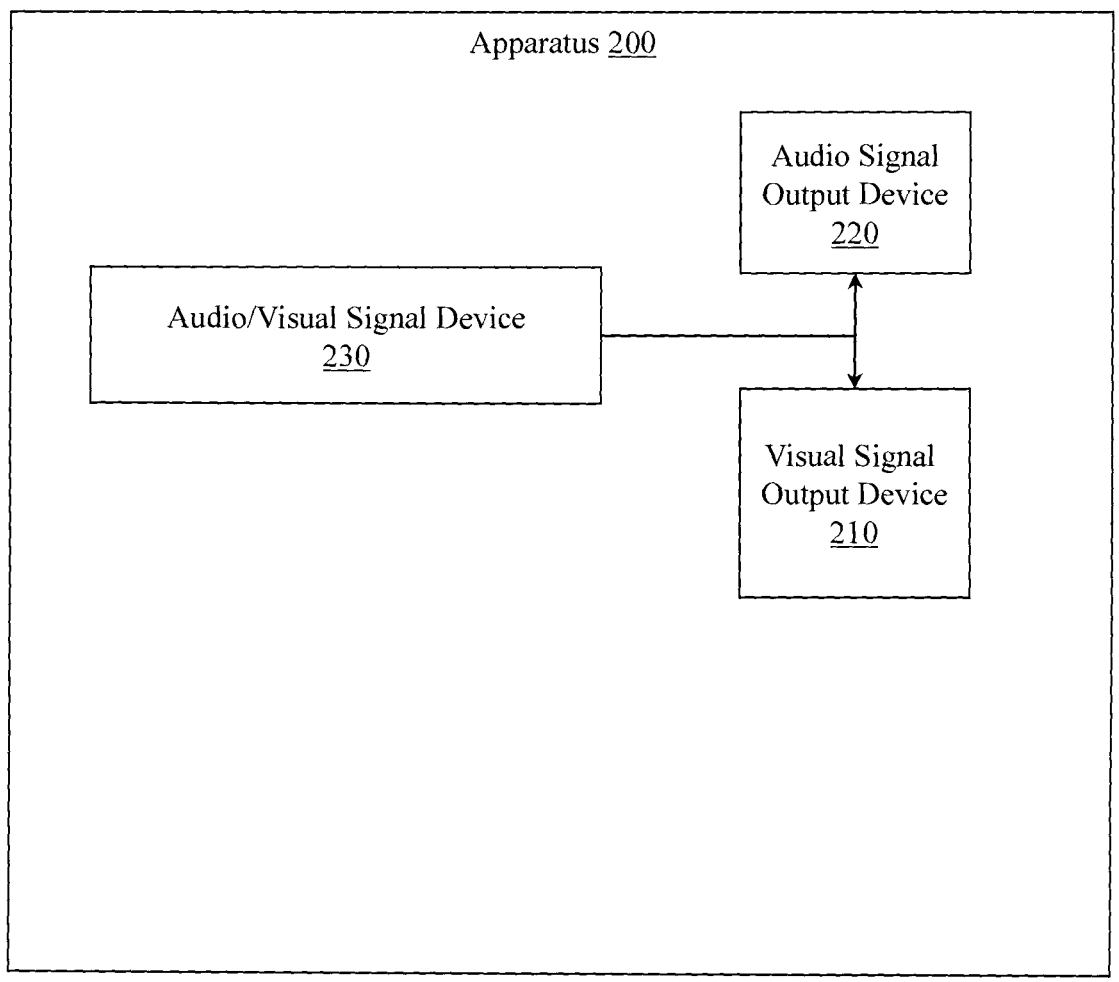
FIG. 2 illustrates an apparatus for low frequency non-invasive sensorial stimulation for seizure control.

FIG. 2 illustrates an apparatus 200 for reducing epileptic seizures in a human patient by non-invasively providing coordinated low frequency audio stimuli and low frequency visual stimuli to the patient. Apparatus 200 includes a visual signal output device 210 that provides an external visual stimulus having a frequency of 1-10 Hz to the visual system of the patient. The external visual stimulus may be produced by, for example, a light emitting diode (LED), an infrared (IR) device, or other device that produces stimuli that can be perceived by the human eye. The external stimulus is provided without mechanical contact with the eye and without electrode penetration of the eye or optic nerve.

Apparatus 200 also includes an audio signal output device 220 that provides an external audible stimulus having a frequency of 1-10 Hz to the hearing system of the patient. The external audible stimulus may be produced by, for example, a speaker, a membrane, a diaphragm, or other device that produces stimuli that can be perceived by the human ear. In one embodiment, the audible signal is embedded in a piece of music or is embedded in random noise. The external stimulus is provided without mechanical contact of the tympanic membrane and without electrode penetration of the cochlear nerve or vestibular nerve.

Apparatus 200 also includes an audio/visual signal device 230 that controls the visual signal output device 210 and the audio signal output device 220 to coordinate the provision of the visual stimulus and the audible stimulus. Coordinating the provision of the visual stimulus and the audible stimulus may include, for example, controlling the times at which the visual stimulus and the audible stimulus are provided, controlling how many presentations of the visual stimulus are made per presentation of the audible stimulus, controlling how many presentations of the audible stimulus are made per presentation of the visible stimulus, or other actions. In one embodiment, the audio/visual signal device 230 synchronizes the audible signal to a piece of music and or to random noise. In one embodiment, the visual signal output device 210 and the audio signal output device 220 are controlled to present the visual stimuli and the audio stimuli so that neural signals generated in response to the visual stimuli and the audio stimuli arrive in target locations within a defined window of time. In one embodiment, apparatus 200 may provide only an audio stimuli or visual stimuli but not both.

In one embodiment, the apparatus 200 may be a single wearable apparatus. For example, apparatus 200 may be embodied in a pair of glasses having sound producing elements near the ears and light producing elements near the eyes. In another embodiment, apparatus 200 may be a headband that wraps around the eyes and ears. The headband may be elasticized and may be suitable for wearing to bed.

In different embodiments, the visual signal output device 210 may be glasses, a mask, an eye patch, a monocle, or a visor. In different embodiments, the audio signal output device 220 may be earphones, an earbud, glasses, or a surface transducer. In one embodiment, to reduce unwanted visual stimulation, the visual signal output device 210 may reduce the spectrum, intensity, or other attribute(s) of external visual stimulation experienced by the patient to a desired stimulation spectrum. Reducing the spectrum, intensity, or other attributes may involve filtering light, blocking light, or otherwise reducing the light presented to the patient other than light from the visual signal output device 210. Similarly, to reduce unwanted audible stimulation, the audio signal output device 220 may perform noise cancellation. Performing noise cancellation may include, for example, reducing the spectrum, amplitude, intensity, or other attributes of sounds presented to the patient other than sounds from the audio signal output device 220.

Figure 3:
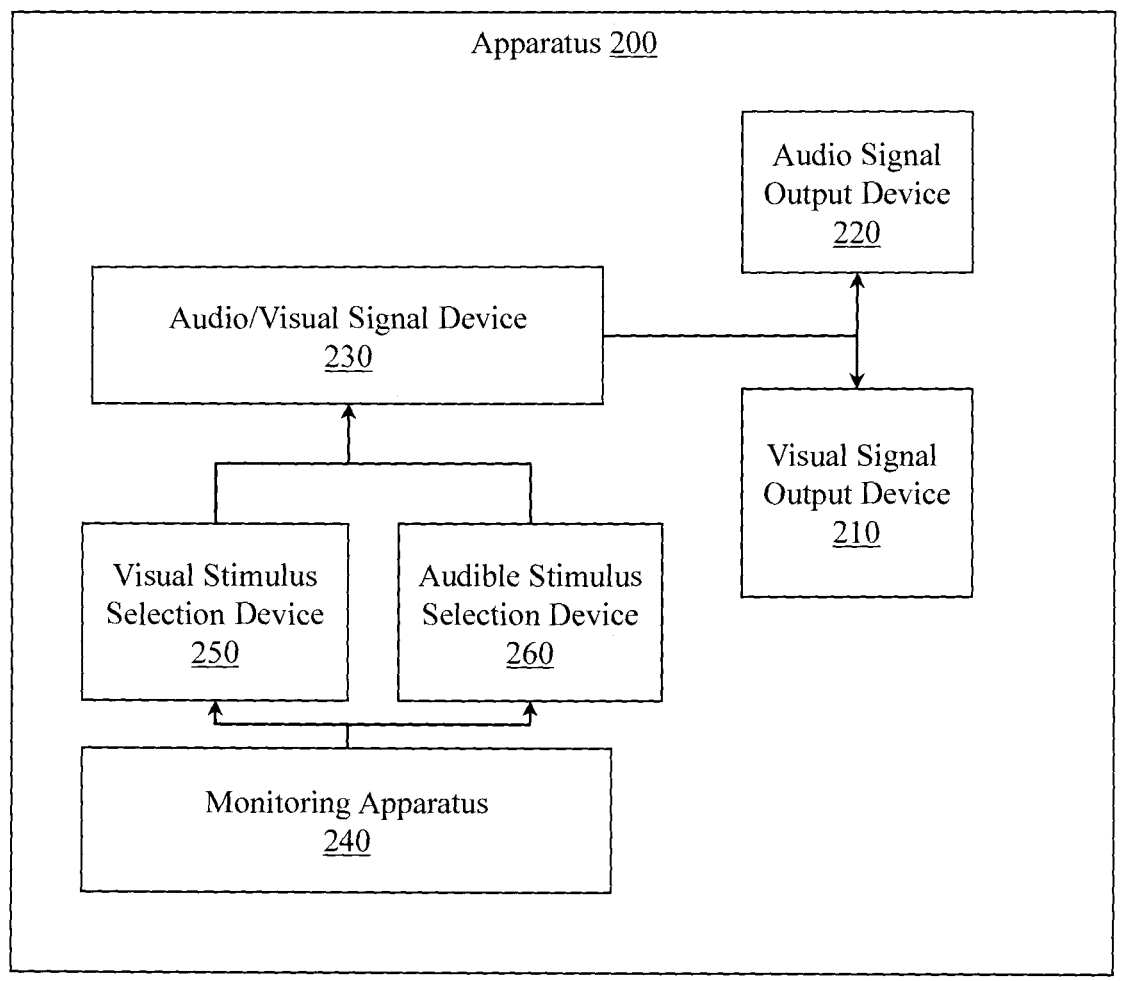
FIG. 3 illustrates an apparatus for low frequency non-invasive sensorial stimulation for seizure control.

FIG. 3 illustrates another embodiment of apparatus 200. This embodiment includes a monitoring apparatus 240 that identifies a state in the brain of the patient. The monitoring apparatus 240 may be, for example, an electroencephalogram (EEG) device. The monitoring apparatus 240 may be configured (e.g., programmed, wired) to identify states including, for example, hyperexcitability in the brain, an imminent epileptic seizure in the patient, an epileptic seizure in progress in the patient, a REM sleep state being experienced by the patient, or a non-REM sleep state being experienced by the patient.

This embodiment of apparatus 200 also includes a visual stimulus selection device 250 that selects the visual stimulus based, at least in part, on the state. Selecting the visual stimulus may include, for example, selecting a frequency for the visual stimulus, selecting an intensity of the visual stimulus, selecting a color for the visual stimulus, or selecting another attribute of the visual stimulus.

This embodiment of apparatus 200 also includes an audio signal selection device 260 that selects the audible stimulus based, at least in part, on the state. Selecting the audible stimulus may include, for example, selecting a frequency for the audible stimulus, selecting an intensity of the audible stimulus, selecting a tone for the audible stimulus, or selecting another attribute of the audible stimulus.

In this embodiment of apparatus 200, since the state of the patient brain may be known, the audio/visual signal device 230 may control the visual signal output device 210 and the audio signal output device 220 to coordinate the provision of the visual stimulus and the audible stimulus based, at least in part, on the state. For example, the number of presentations of the visual stimulus compared to the number of presentations of the audible stimulus may be adjusted, the time interval between presentations of the stimuli may be adjusted, and other coordination parameters may be adjusted. Based on the state, only a visual stimulus or an audible stimulus but not both may be provided.

In one embodiment, apparatus 200 may also include a direct stimulation control circuit that controls direct stimulation of a sensory nerve of the patient. In this embodiment, the audio/visual signal device 230 may coordinate the direct stimulation with the visual stimuli or the audio stimuli.

Figure 4:
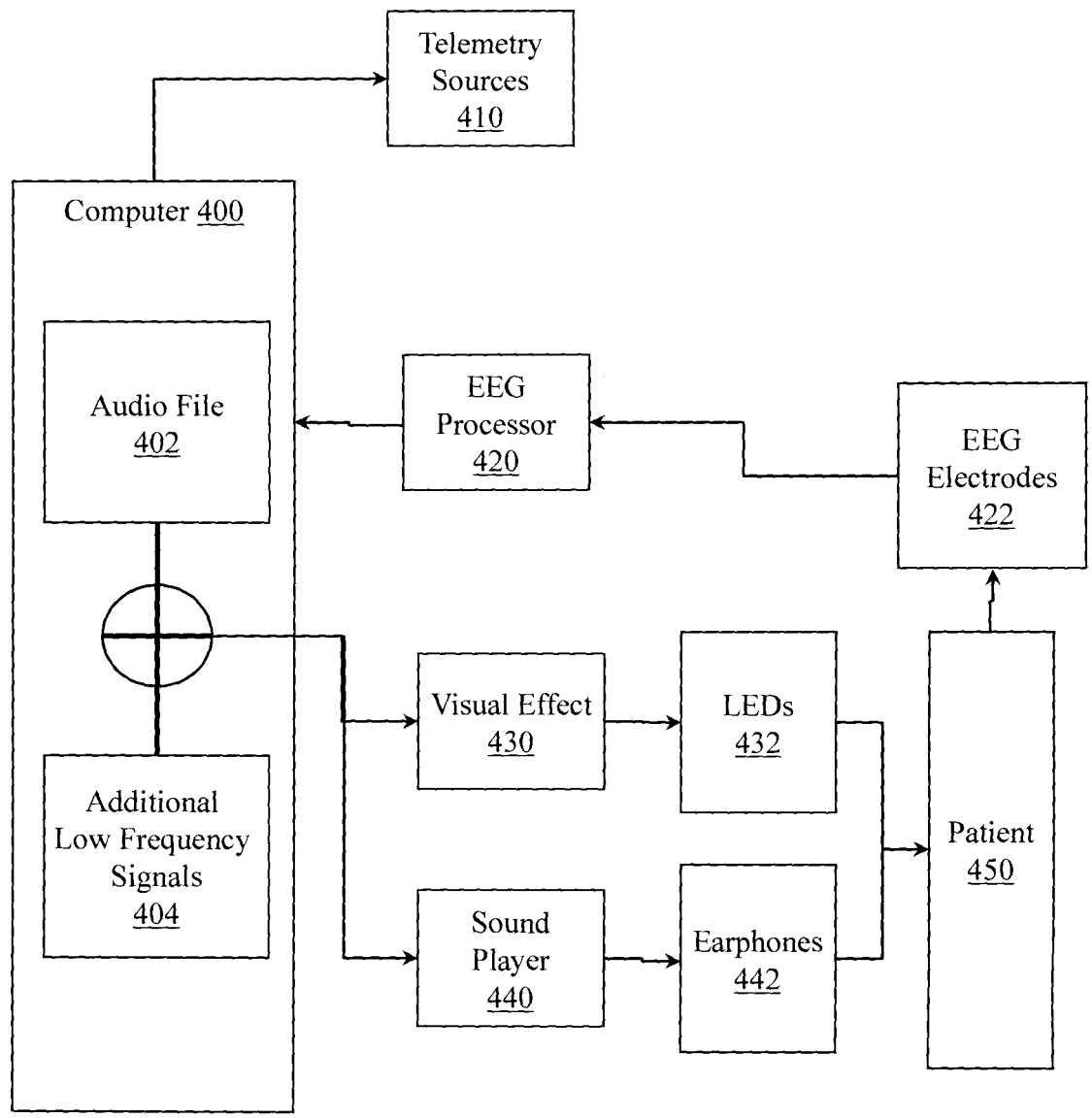
FIG. 4 illustrates a system for low frequency non-invasive sensorial stimulation for seizure control.

FIG. 4 illustrates a computer 400 that is part of a system for providing low-frequency non-invasive sensorial stimulation for seizure control. Computer 400 may store an audio file 402 and additional low frequency signals 404 that may be combined and provided by computer 400. The low frequency signals 404 may be in the range of 1-10 Hz. Computer 400 may provide sounds generated from the audio file 402 and the additional low frequency signals 404 to a sound player 440. Sound player 440 may in turn provide signals to earphones 442. The signals provided to earphones 442 may be signals from which audible sounds can be provided to a patient 450.

Computer 400 may also provide signals to a visual effect apparatus or circuit 430. The visual effect element 430 may in turn provide signals to an output device (e.g., light emitting diodes 432) from which visible stimuli can be provided to patient 450. Computer 400 may provide the signals to the sound player 440 and to the visual effect circuit 430 in a manner that facilitates controlling how and when the earphones 442 and LEDs 432 provide the audible and visual stimuli to the patient 450. For example, the ratio of visual stimuli to audible stimuli may be controlled by computer 400. Similarly, the relative intensities of the visual stimuli and audible stimuli may be controlled by computer 400. In one embodiment, the signals may be provided to the patient 450 with no feedback. In another embodiment, the patient 450 may be monitored by, for example, EEG electrodes 422. The EEG electrodes 422 may provide signals to an EEG processor 420 that in turn provides signals to the computer 400. Computer 400 may then use the feedback from the patient 450 to control how subsequent signals are provided to the visual effect circuit 430 or the sound player 440. In one embodiment, computer 400 may also provide output signals to various telemetry sources 410 that may be monitoring or otherwise tracking the patient 450 or the computer 400.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 5:
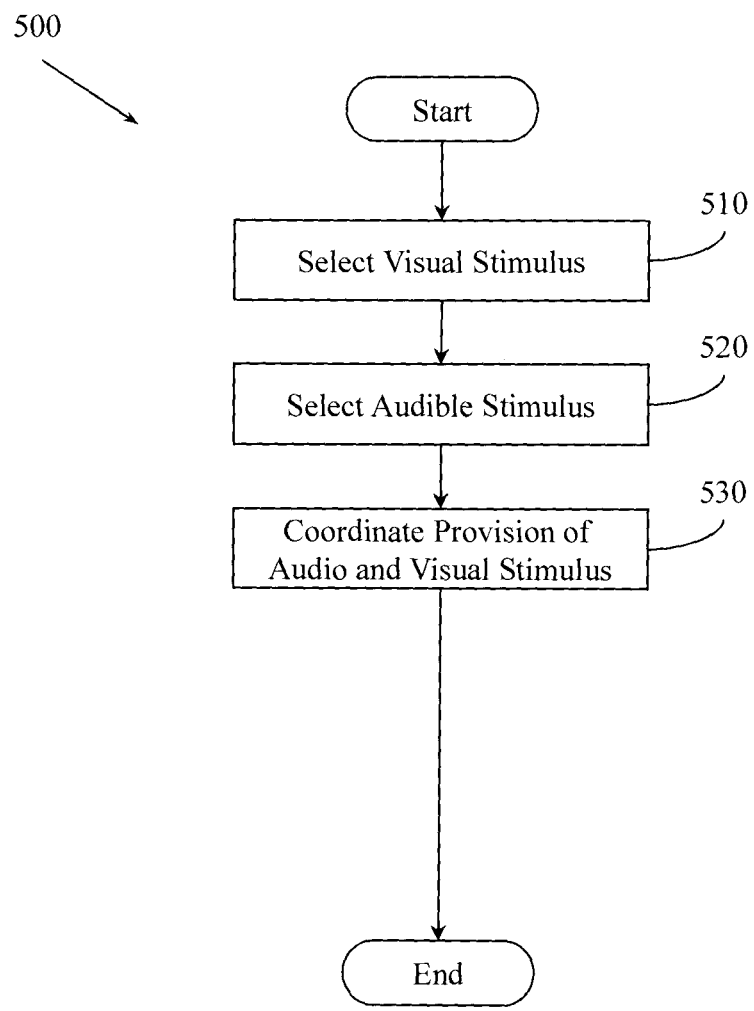
FIG. 5 illustrates an example method for low frequency non-invasive sensorial stimulation for seizure control.

FIG. 5 illustrates an example method 500 for low frequency non-invasive sensorial stimulation for seizure control. Method 500 facilitates reducing epileptic seizures in a human patient. Method 500 includes, at 510, selecting a visual stimulus to provide to the patient. The visual stimulus may be a visible light or otherwise detectable spectra (e.g., infrared) comprising a plurality of illuminations displayed at 1-10 Hz. Method 500 also includes, at 520, selecting an audible stimulus to provide to the patient. The audible stimulus is an audible sound comprising a plurality of sounds presented at 1-10 Hz. The sounds may include, for example, a click. In one embodiment, the audible stimulus may be embedded in a piece of music. In another embodiment, the audible stimulus may be embedded in random noise.

Method 500 also includes, at 530, coordinating the providing of the visual stimulus and the audible stimulus. Coordinating the providing of the visual stimulus and the audible stimulus may include, for example, causing the two stimuli to be provided at the same time, causing the two stimuli to be provided in an alternating fashion, causing just one of the stimuli to be provided, or providing the two stimuli to be provided in different patterns with different numbers of presentations and different timings between presentations. Coordinating the providing of the two stimuli may include, for example, controlling a time interval between applications of the different stimuli, controlling how many of one stimuli are provided per instance of the other stimuli, controlling the relative intensity of the different stimuli, or other actions.

Figure 6:
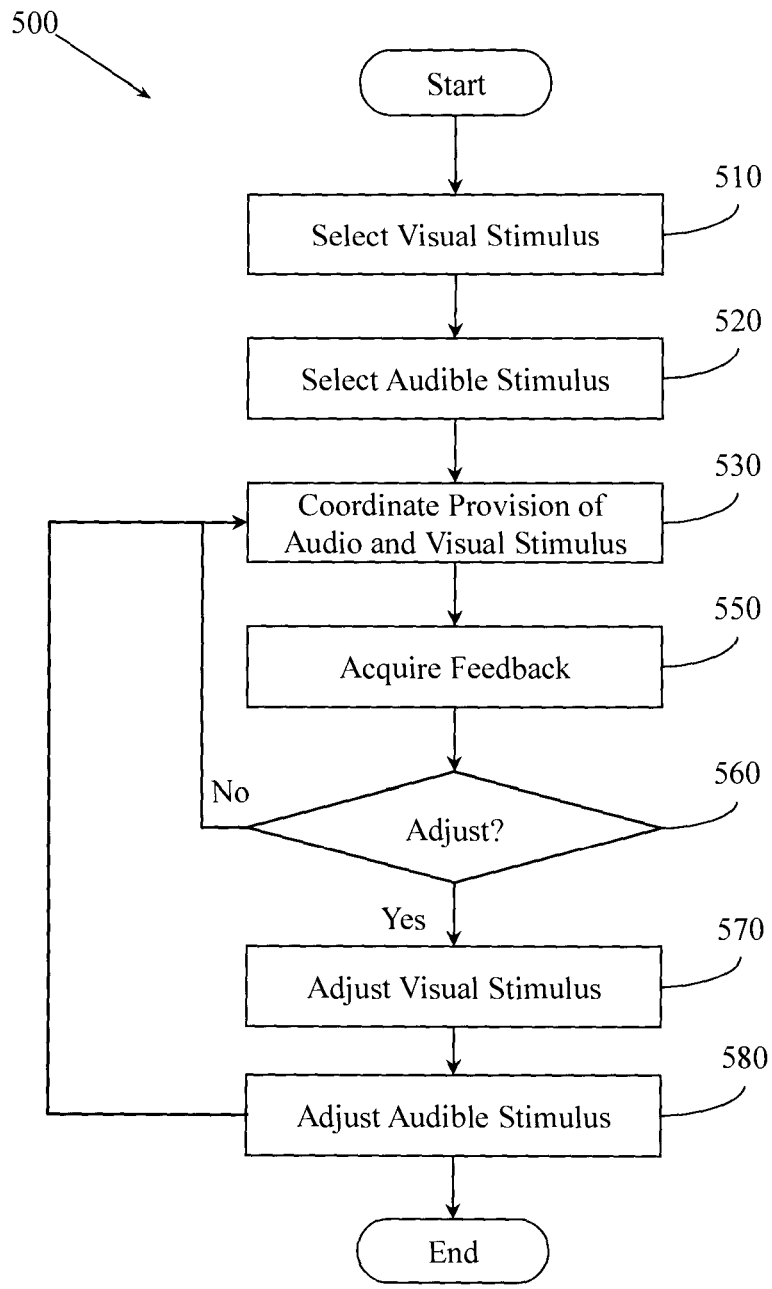
FIG. 6 illustrates an example method for low frequency non-invasive sensorial stimulation for seizure control.

FIG. 6 illustrates another embodiment of method 500. This embodiment also includes, at 550, acquiring feedback from the brain of the patient. In one embodiment, acquiring the feedback may include detecting an EEG signal from the human patient. The EEG signal may indicate a state in the brain of the patient. The state may be, for example, hyperexcitability, an imminent epileptic seizure, an ongoing epileptic seizure, a REM sleep state, a non-REM sleep state, or another state.

Once the state is determined from the EEG signal, method 500 may continue, at 560, to make a determination about whether to adjust the visual stimulus, the audible stimulus, or how the visual stimulus and audible stimulus are coordinated. If the determination at 560 is no, then method 500 may return to 530. But if the determination at 560 is yes, then method 500 may proceed, at 570, by manipulating the visual stimulus based, at least in part, on the state. Method 500 may then proceed, at 580, by manipulating the audible stimulus based, at least in part, on the state. Once the visual stimulus and audible stimulus have been adjusted, method 500 may return to 530 and selectively manipulate the coordinating of the visual stimulus and the audible stimulus based, at least in part, on the state. Adjusting the visual stimulus may include, for example, changing the frequency of the visual stimulus, changing the intensity of the visual stimulus, changing a pattern in which the visual stimulus is provided, stopping the visual stimulus, or other changes. Adjusting the audible stimulus may include, for example, changing the frequency of the audible stimulus, changing the intensity of the audible stimulus, changing a pattern in which the audible stimulus is provided, stopping the audible stimulus, or other changes. Adjusting the coordination between the visual stimulus and the audible stimulus may include, for example, changing the temporal relationship between when the different stimuli are provided.

In one embodiment, method 500 may take active steps to alter the environment in which the visual stimulus and audible stimulus are provided. For example, method 500 may include controlling an apparatus to selectively block or otherwise limit undesired visual stimulation to the patient or to selectively block or otherwise limit undesired audible stimulation to the patient.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Logic", as used herein, includes but is not limited to hardware, firmware, software in execution on a machine, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A system comprising:
   a visual signal output device configured to provide an external visual stimulus to a visual system of a patient, wherein the external visual stimulus comprises a low frequency;
   an audio signal output device configured to provide an external audible stimulus to a hearing system of the patient, wherein the external audible stimulus comprises the low frequency and is incorporated into music or random background noise; and an audio/visual signal device configured to coordinate presentation of the external visual stimulus and the external audible stimulus to the subject based on a state of the patient.

2. The system of claim 1, wherein the low frequency is from 1 to 10 Hertz.

3. The system of claim 1, wherein the state of the patient is determined from an electroencephalogram (EEG) signal acquired from the patient.

4. The system of claim 1, wherein the state of the patient comprises at least one of hyperexcitability, imminent epileptic seizure, epileptic seizure in progress, and rapid eye movement sleep.

5. The system of claim 1, further comprising a wearable apparatus that comprises at least one of the visual signal output device and the audio signal output device.

6. The system of claim 5, wherein the wearable apparatus comprises EEG equipment to monitor the state of the patient.

7. The system of claim 6, wherein the audio/visual signal device coordinates the presentation of the external visual stimulus and the external audible stimulus in response to the state of the patient determined based on an EEG signal from the EEG equipment.

8. The system of claim 1, wherein audio/visual signal device coordinates the presentation by providing only the external visual stimulus or the external audible stimulus to the patient at a time.

9. The system of claim 1, wherein the audio/visual signal device coordinates at least one of duration, timing, and the low frequency of the external visual stimulus and the external audible stimulus.

10. The system of claim 1, wherein the visual signal output device comprises at least one of a light emitting diode or an infrared device.

11. A method comprising:
determining, by a system comprising a processor, a state of a patient based on a previously recorded conduction data;
configuring, by the system, an audible stimulus and a visual stimulus with a low frequency, wherein the audible stimulus is provided as part of a piece of music or within random noise;
applying, by the system, the audible stimulus and the visual stimulus to the patient in a coordinated manner based on the previously recorded conduction data.

12. The method of claim 11, further comprising recording the conduction data.

13. The method of claim 12, wherein the conduction data is EEG data.

14. The method of claim 11, wherein the state comprises at least one of hyperexcitability, imminent epileptic seizure, epileptic seizure in progress, and rapid eye movement sleep.

15. The method of claim 11, wherein the low frequency is from 1 to 10 Hertz.

16. The method of claim 11, further comprising reconfiguring the audible stimulus or the visual stimulus based on a change in state of the patient.

17. The method of claim 11, further comprising manipulating the manner in which the visual stimulus ad the audible stimulus are coordinated based on the state.

18. The method of claim 11, further comprising blocking, by the system, undesired visual stimulation or audible stimulation.

19. The method of claim 11, wherein the system comprises a wearable apparatus to output the visual stimulus and the audible stimulus.

20. The method of claim 11, wherein the applying comprises applying only the audible stimulus or the visual stimulus for a time.

* * * * *